(12) United States Patent
Bradley et al.

(10) Patent No.: US 11,135,424 B2
(45) Date of Patent: Oct. 5, 2021

(54) APPARATUS, SYSTEM, AND METHOD FOR TARGETED PLACEMENT OF A PERCUTANEOUS ELECTRODE

(71) Applicant: Greatbatch Ltd., Clarence, NY (US)

(72) Inventors: Kerry Bradley, Glendale, CA (US); Leslie I. Halberg, Valencia, CA (US)

(73) Assignee: Greatbatch Ltd., Clarence, NY (US)

( * ) Notice: Subject to any disclaimer, the term of this patent is extended or adjusted under 35 U.S.C. 154(b) by 1283 days.

(21) Appl. No.: 14/320,898

(22) Filed: Jul. 1, 2014

(65) Prior Publication Data

US 2015/0011871 A1  Jan. 8, 2015

Related U.S. Application Data

(60) Provisional application No. 61/841,965, filed on Jul. 2, 2013.

(51) Int. Cl.
*A61N 1/05* (2006.01)
*A61B 5/06* (2006.01)
(Continued)

(52) U.S. Cl.
CPC ............ *A61N 1/0551* (2013.01); *A61B 5/064* (2013.01); *A61B 8/0841* (2013.01); *A61N 1/05* (2013.01); *A61N 1/0553* (2013.01); *A61N 1/36017* (2013.01); *A61N 1/36021* (2013.01); *A61N 1/36071* (2013.01); *A61N 1/36125* (2013.01); *A61N 1/36139* (2013.01); *A61N 1/36146* (2013.01); *A61N 1/36153* (2013.01);
(Continued)

(58) Field of Classification Search
CPC ...... A61N 1/05; A61N 1/0551; A61N 1/0553; A61N 1/36017; A61N 1/36021; A61N 1/36071; A61N 1/36125; A61N 1/36143; A61N 1/36153; A61N 1/37223; A61N 1/37252; A61N 1/3787; A61N 1/0558; A61B 5/064; A61B 8/0841; A61B 17/3468; A61M 2025/09125
See application file for complete search history.

(56) References Cited

U.S. PATENT DOCUMENTS 5,228,455 A * 7/1993 Barcel .................... A61N 1/056
600/377
5,255,691 A   10/1993 Otten
(Continued)

FOREIGN PATENT DOCUMENTS

RU         72856      3/2011
WO      2005055849    6/2005

*Primary Examiner* — Christopher Koharski
*Assistant Examiner* — Katherine M McDonald
(74) *Attorney, Agent, or Firm* — Michael P. Horvath

(57) ABSTRACT

In various examples, an apparatus is configured for targeted placement of a lead body within a patient. The lead body includes at least one distal electrode. The apparatus includes a needle including a lumen sized to accommodate the lead body within the lumen. A stylet is insertable within the needle, wherein at least one of the needle and the stylet includes at least one imageable marker corresponding in size, shape, and location to the at least one distal electrode of the lead body. The at least one imageable marker is configured to allow a user to determine placement within the patient of the at least one distal electrode of the lead body prior to implantation of the lead body within the patient.

20 Claims, 3 Drawing Sheets

(51) Int. Cl.
  *A61B 8/08* (2006.01)
  *A61N 1/36* (2006.01)
  *A61N 1/372* (2006.01)
  *A61N 1/378* (2006.01)
  *A61N 1/375* (2006.01)

(52) U.S. Cl.
  CPC ......... *A61N 1/3752* (2013.01); *A61N 1/3787* (2013.01); *A61N 1/37223* (2013.01); *A61N 1/37235* (2013.01); *A61N 1/37252* (2013.01)

(56) References Cited

U.S. PATENT DOCUMENTS

| | | | |
|---|---|---|---|
| 5,876,408 A * | 3/1999 | Alt | A61N 1/056 606/129 |
| 6,516,227 B1 * | 2/2003 | Meadows | A61N 1/36071 607/46 |
| 7,949,408 B2 | 5/2011 | Bonde et al. | |
| 7,976,469 B2 | 7/2011 | Bonde et al. | |
| 8,611,993 B2 | 12/2013 | Vitullo et al. | |
| 8,690,776 B2 | 4/2014 | Razzaque et al. | |
| 2002/0147484 A1 * | 10/2002 | Dahl | A61N 1/056 607/116 |
| 2003/0009207 A1 * | 1/2003 | Paspa | A61N 1/0529 607/116 |
| 2005/0021119 A1 * | 1/2005 | Sage | A61N 1/0529 607/122 |
| 2005/0288685 A1 | 12/2005 | Gulles et al. | |
| 2008/0103569 A1 * | 5/2008 | Gerber | A61N 1/05 607/115 |
| 2008/0132979 A1 * | 6/2008 | Gerber | A61N 1/0526 607/116 |
| 2008/0269716 A1 * | 10/2008 | Bonde | A61B 17/3468 604/506 |
| 2009/0275997 A1 * | 11/2009 | Faltys | A61N 1/0553 607/2 |
| 2011/0208157 A1 | 8/2011 | Geliebter et al. | |
| 2011/0276001 A1 | 11/2011 | Schultz et al. | |
| 2012/0016378 A1 * | 1/2012 | Pianca | A61N 1/36182 606/129 |
| 2012/0197372 A1 * | 8/2012 | Burgher | A61N 1/0558 607/118 |
| 2012/0330184 A1 | 12/2012 | Mahapatra et al. | |
| 2013/0072900 A1 | 3/2013 | Colantonio | |
| 2013/0072941 A1 | 3/2013 | Tan-Malecki et al. | |
| 2013/0096428 A1 | 4/2013 | Gillies et al. | |
| 2013/0109910 A1 | 5/2013 | Alexander et al. | |
| 2013/0110210 A1 * | 5/2013 | North | A61N 1/0553 607/117 |
| 2014/0018732 A1 * | 1/2014 | Bagaoisan | A61M 25/0136 604/95.04 |

* cited by examiner

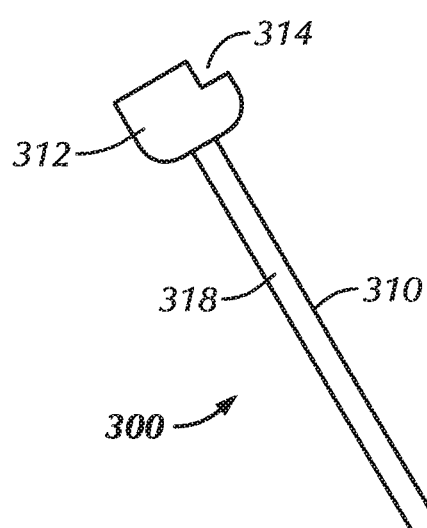
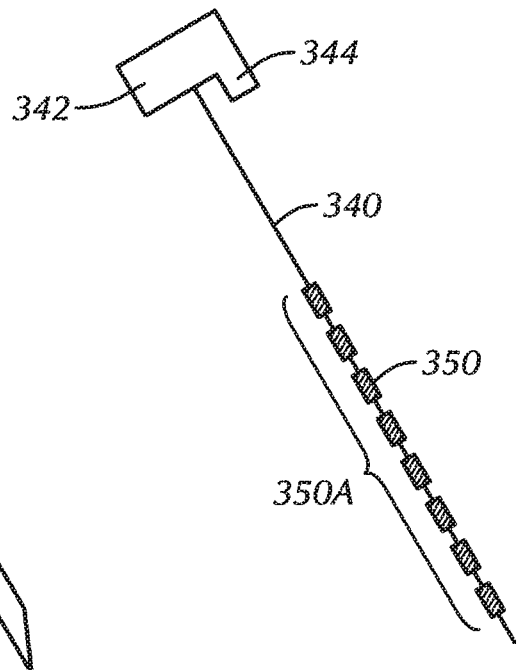
FIG. 3A  FIG. 3B
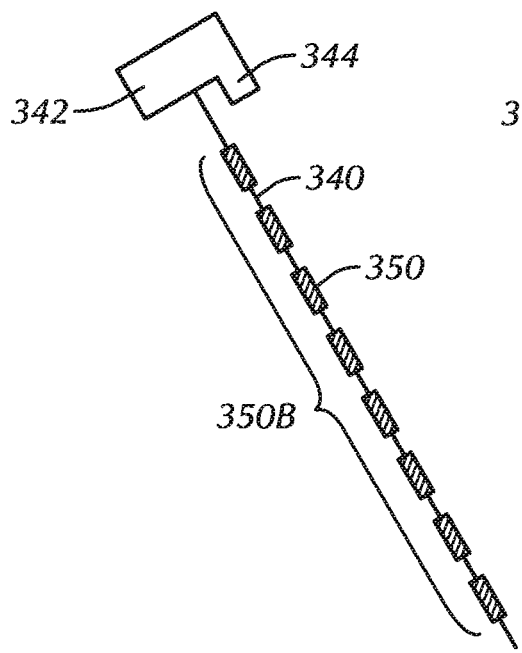
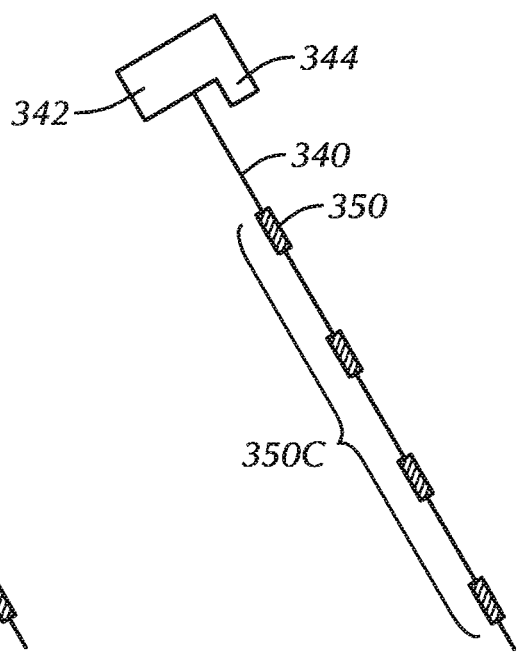
FIG. 3C  FIG. 3D

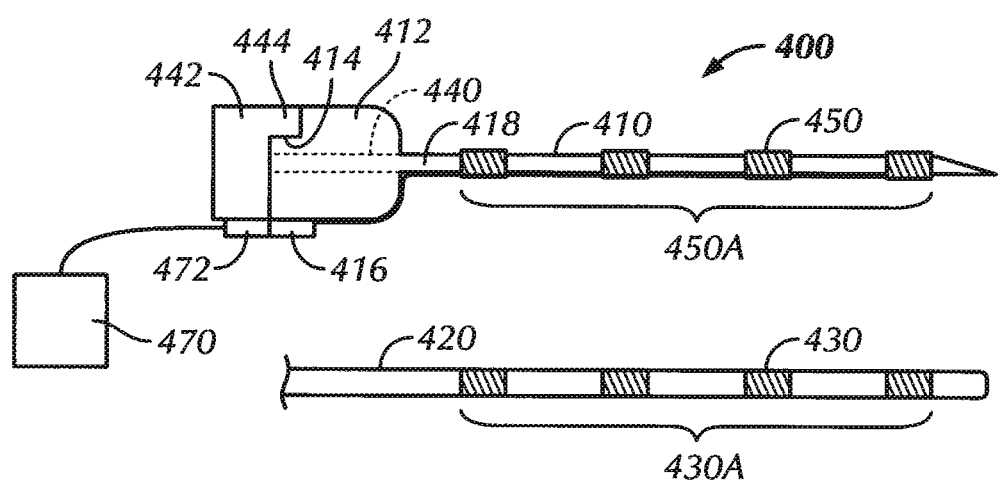
FIG. 4
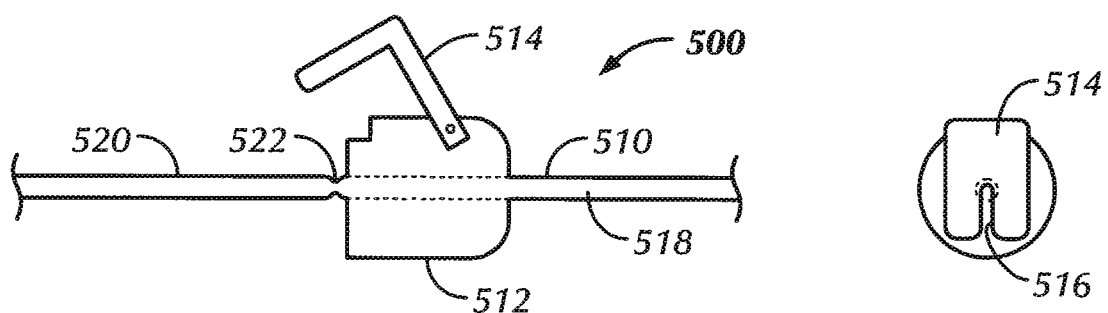
FIG. 5A   FIG. 5B

APPARATUS, SYSTEM, AND METHOD FOR TARGETED PLACEMENT OF A PERCUTANEOUS ELECTRODE

CROSS REFERENCE TO RELATED APPLICATIONS

This application claims the benefit of priority to U.S. Provisional Application Ser. No. 61/841,965, filed on Jul. 2, 2013, entitled "STIMULATION APPARATUSES, DEVICES, SYSTEMS, AND METHODS," which is incorporated by reference herein in its entirety.

TECHNICAL FIELD

The present patent document pertains generally to targeting locations within a patient and more particularly, but not by way of limitation, to an apparatus, system, and method for targeted placement of an implantable device within a patient.

BACKGROUND

Placement and implant of in-line electrodes via a percutaneous needle can be a simple, minimally invasive procedure, especially when performed with ultrasound guidance.

The typical placement technique for peripheral nerve stimulation involves imaging the nerve in a short-axis view using ultrasound guidance, and then introducing the needle at approximately a right angle to the axis of the nerve, where the tip of the needle reaches a few millimeters beyond the nerve.

The stylet of the needle is then withdrawn and the lead is threaded down the bore of the needle until the tip of the lead reaches the tip of the needle. Next, the needle is withdrawn from the tissue over the lead body. Test stimulation is then commenced to determine paresthesia coverage for the patient using a variety of contact choices and stimulation parameters.

While simple, if the lead is not in an optimal position, it may not be trivial to reintroduce the needle to the tissue to allow for lead placement adjustment. For instance, sliding the needle back over the lead could result in tissue coring or other further trauma, or the needle could shave or nick the lead. Getting the lead to a better position relative to the nerve may then involve another needle stick to better target the nerve.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used to target placement of an implantable device within a patient. The present inventors have further recognized, among other things, that the subject matter can be used with an electrical lead delivery system to target placement of an electrical stimulation lead. To better illustrate the apparatuses, systems, and methods described herein, a non-limiting list of examples is provided here:

Example 1 can include subject matter that can include an apparatus configured for targeted placement of a lead body within a patient. The lead body includes at least one distal electrode. The apparatus includes a needle including a lumen sized to accommodate the lead body within the lumen. A stylet is insertable within the needle, wherein at least one of the needle and the stylet includes at least one imageable marker corresponding in size, shape, and location to the at least one distal electrode of the lead body. The at least one imageable marker is configured to allow a user to determine placement within the patient of the at least one distal electrode of the lead body prior to implantation of the lead body within the patient.

In Example 2, the subject matter of Example 1 is optionally configured such that the needle includes the at least one imageable marker.

In Example 3, the subject matter of Example 2 is optionally configured such that the needle includes a plurality of imageable markers. The plurality of imageable markers correspond in size, shape, and location to a plurality of distal electrodes of the lead body.

In Example 4, the subject matter of Example 3 optionally includes another needle including another plurality of imageable markers. The other plurality of imageable markers correspond in size, shape, and location to another plurality of distal electrodes of another lead body. The other plurality of distal electrodes of the other lead body is configured differently than the plurality of distal electrodes of the lead body.

In Example 5, the subject matter of any one of Examples 24 is optionally configured such that the at least one imageable marker of the needle includes a needle electrode configured to perform a test stimulation.

In Example 6, the subject matter of any one of Examples 1-5 is optionally configured such that the stylet includes the at least one imageable marker.

In Example 7, the subject matter of Example 6 is optionally configured such that the stylet includes a plurality of imageable markers. The plurality of imageable markers correspond in size, shape, and location to a plurality of distal electrodes of the lead body.

In Example 8, the subject matter of Example 7 optionally includes another stylet including another plurality of imageable markers. The other plurality of imageable markers corresponding in size, shape, and location to another plurality of distal electrodes of another lead body. The other plurality of distal electrodes of the other lead body is configured differently than the plurality of distal electrodes of the lead body.

In Example 9, the subject matter of any one of Examples 1-8 is optionally configured such that the at least one imageable marker is echogenic. The at least one imageable marker is configured to be imaged by an ultrasound technique.

In Example 10, the subject matter of any one of Examples 1-9 is optionally configured such that the at least one imageable marker is configured to be imaged by a fluoroscopy technique.

Example 11 can include, or can optionally be combined with any one of Examples 1-10 to include subject matter that can include an apparatus for targeted placement of a first lead body within a patient. The first lead body includes a first plurality of distal electrodes. The apparatus includes a first needle including a lumen sized to accommodate the first lead body within the lumen. A first stylet is insertable within the needle, wherein at least one of the first needle and the first stylet includes a first plurality of imageable markers corresponding in size, shape, spacing, and location to the first plurality of distal electrodes of the first lead body. The first plurality of imageable markers is configured to allow a user to determine placement within the patient of the first plurality of distal electrodes of the first lead body prior to implantation of the first lead body within the patient.

In Example 12, the subject matter of Example 11 is optionally configured such that the first plurality of imageable markers is echogenic. The first plurality of imageable markers is configured to be imaged by an ultrasound technique.

In Example 13, the subject matter of any one of Examples 11-12 is optionally configured such that the first plurality of imageable markers is configured to be imaged by a fluoroscopy technique.

In Example 14, the subject matter of any one of Examples 11-13 is optionally configured such that the first needle includes the first plurality of imageable markers. Each of the first plurality of imageable markers of the first needle includes a needle electrode configured to perform a test stimulation.

In Example 15, the subject matter of any one of Examples 11-14 is optionally configured such that the first needle includes the first plurality of imageable markers. The apparatus includes a second needle interchangeable with the first needle. The second needle includes a second plurality of imageable markers differently configured in at least one of size, shape, spacing, and location from the first plurality of imageable markers of the first needle, wherein the second plurality of imageable markers correspond in size, shape, spacing, and location to a second plurality of distal electrodes of a second lead body.

In Example 16, the subject matter of any one of Examples 11-15 is optionally configured such that the first stylet includes the first plurality of imageable markers. The apparatus including a second stylet interchangeable with the first stylet. The second stylet includes a second plurality of imageable markers differently configured in at least one of size, shape, spacing, and location from the first plurality of imageable markers of the first stylet, wherein the second plurality of imageable markers correspond in size, shape, spacing, and location to a second plurality of distal electrodes of a second lead body.

Example 17 can include, or can optionally be combined with any one of Examples 1-16 to include subject matter that can include an apparatus for targeted placement of a first lead body within a patient. The first lead body includes a first plurality of distal electrodes. The apparatus includes a first needle including a lumen sized to accommodate the first lead body within the lumen. A first stylet is insertable within the needle, wherein at least one of the first needle and the first stylet includes a first plurality of echogenic markers corresponding in spacing and location to the first plurality of distal electrodes of the first lead body. The first plurality of echogenic markers is configured to allow a user to image the first plurality of echogenic markers by an ultrasonic technique to determine placement within the patient of the first plurality of distal electrodes of the first lead body prior to implantation of the first lead body within the patient.

In Example 18, the subject matter of Example 17 is optionally configured such that the first needle includes the first plurality of echogenic markers. Each of the first plurality of echogenic markers of the first needle includes a needle electrode configured to perform a test stimulation.

In Example 19, the subject matter of any one of Examples 17-18 is optionally configured such that the first needle includes the first plurality of echogenic markers. The apparatus includes a second needle interchangeable with the first needle. The second needle includes a second plurality of echogenic markers differently configured in at least one of spacing and location from the first plurality of echogenic markers of the first needle, wherein the second plurality of echogenic markers correspond in spacing and location to a second plurality of distal electrodes of a second lead body.

In Example 20, the subject matter of any one of Examples 17-18 is optionally configured such that the first stylet includes the first plurality of echogenic markers. The apparatus includes a second stylet interchangeable with the first stylet. The second stylet includes a second plurality of echogenic markers differently configured in at least one of spacing and location from the first plurality of echogenic markers of the first stylet, wherein the second plurality of echogenic markers correspond in spacing and location to a second plurality of distal electrodes of a second lead body.

BRIEF DESCRIPTION OF THE DRAWINGS

FIGS. 3A-3D show a tissue targeting apparatus in accordance with at least one example of the invention.

FIG. 4 shows a tissue targeting apparatus in accordance with at least one example of the invention.

FIGS. 5A and 5B show a tissue targeting apparatus in accordance with at least one example of the invention.

DETAILED DESCRIPTION

The present patent document relates to apparatuses, systems, and methods for targeted placement of an implantable device within a patient. For instance, the apparatuses, systems, and methods of the present patent document can be used, in some examples, to target placement of an electrical stimulation lead.

The present inventors have recognized, among other things, that it is desirable to target placement of an implantable device within a patient to allow for better placement of the implantable device and potentially improve performance of the implantable device in treating the patient. The present inventors have further recognized, among other things, that it is desirable to provide an electrical lead delivery apparatus, system, and method for targeting placement of an electrical stimulation lead. While primarily described with respect to targeted placement of neurostimulation leads, it should be understood, however, that the subject matter described herein can be used with other implantable medical devices.

Some embodiments include apparatuses, systems, and methods for optimally targeting tissues to be stimulated with in-line electrodes. In some embodiments, an apparatus includes a needle system for electrode lead delivery with various features, imagable and/or electrical, which allow for confirmation of the final stimulating electrode position relative to the targeted tissue prior to removal of the delivery needle.

Referring to FIGS. 1A-5B, and in some embodiments, the system includes a needle which is configured to permit contact or electrode visualization on percutaneous electrodes as they reside within the bore of the needle. In some embodiments, such visualization can be provided by any standard medical imaging technique, such as, for instance, one or more of x-ray techniques, fluoroscopy techniques, ultrasound techniques, etc.

Figure 1A:
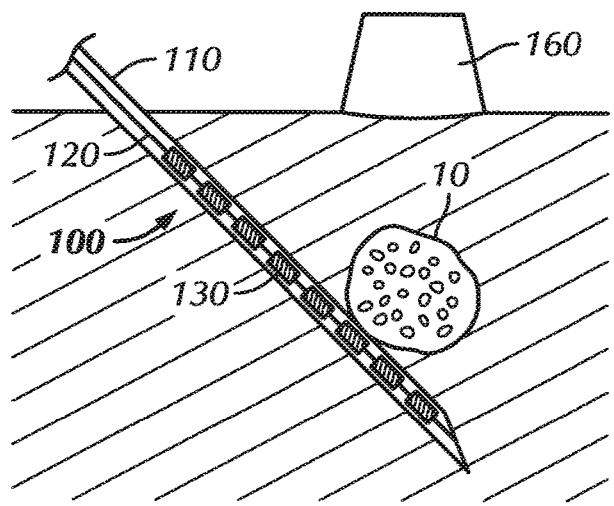
FIGS. 1A and 1B show a tissue targeting apparatus in accordance with at least one example of the invention.
Figure 1B:
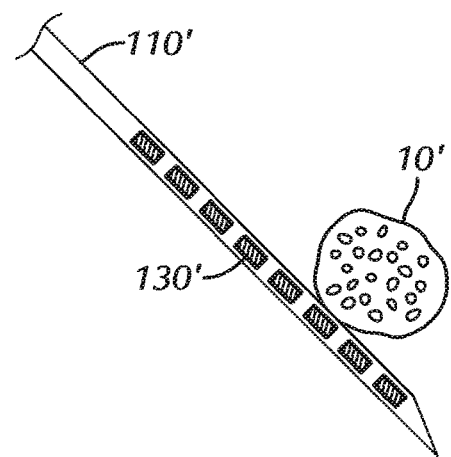

Referring to FIGS. 1A and 1B, and in some embodiments, an apparatus 100 is configured for targeted placement of a lead body 120 within a patient. In some examples, the apparatus 100 includes a needle 110 that is formed of a material that is nominally visible in the particular imaging mode (including, but not limited to ultrasound, fluoroscopy, magnetic resonance imaging (MRI), computerized tomography, x-ray, etc.), yet still provides sufficient image detail to allow for accurate visualization during placement. In some embodiments, distal contacts or electrodes 130 on a lead body 120 are highly visible with the employed imaging technique such that they can easily be seen or imaged while positioned within the needle 110. In some embodiments, the distal contacts or electrodes 130 on the lead are physically etched or otherwise modified or treated to increase their echogenicity in a multitude of imaging planes which may be experienced targeting various tissue or nerves.

In some examples, the apparatus 100 is used with ultrasound imaging. That is, in some examples, the lead body 120 includes one or more distal electrodes 130 that are visible in the ultrasound imaging mode. In some examples, using an ultrasound transducer 160, a physician or other user can place the needle 110 with the lead body 120 (having ultrasound-visible distal electrodes 130) inside to a desired location proximate a nerve 10 within a patient. During placement, in some examples, the physician or other user can view an ultrasound image (FIG. 2B) to track a distal electrode image 130' and a needle image 110' in order to place the distal electrode image 130' in a desired location with respect to a nerve image 10'. In some examples, imaging (ultrasound or other modes) is done real-time to allow for real-time location tracking of the needle 110 and distal electrodes 130. In this way, in some examples, the physician or other user can track the distal electrodes 130 with respect to the nerve 10 or other target and determine the optimal or otherwise desired location of the one or more distal electrodes 130 with respect to the nerve 10 or other target. For instance, the physician or other user can place one or more particular distal electrodes 130 proximate the nerve 10 or other target, orient the distal electrodes 130 with respect to the nerve 10 or other target in a manner such that a maximum number of distal electrodes 130 are disposed proximate the nerve 10 or other target, and/or determine whether a particular pattern of distal electrodes 130 is desirable for a particular nerve 10 or other target.

Figure 2A:
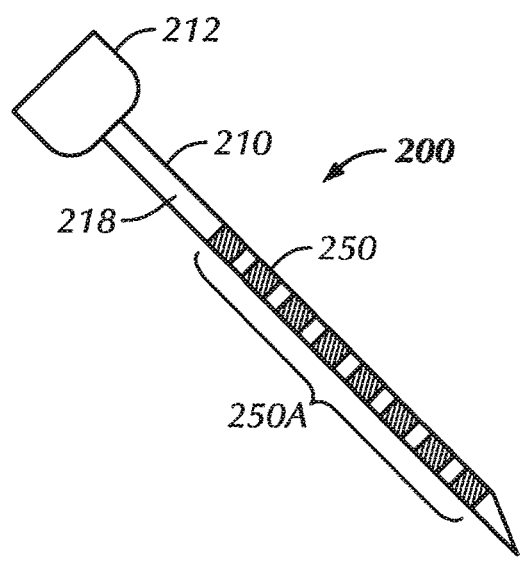
FIGS. 2A and 2B show tissue targeting apparatuses in accordance with at least one example of the invention.
Figure 2B:
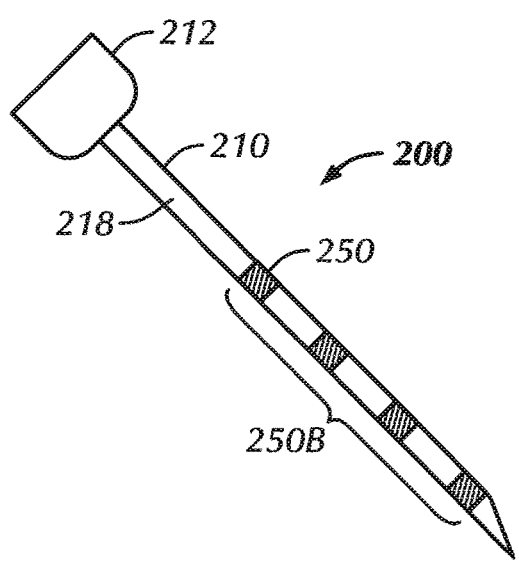

Referring to FIGS. 2A and 2B, in some embodiments, an apparatus 200 is configured for targeted placement of a lead body within a patient. In some examples, the lead body is similar to the lead body 120 described herein. In some examples, the lead body includes at least one distal electrode. In some examples, the apparatus 200 includes a needle 210 including a needle head 212 and a lumen 218 through the needle 210. In some examples, the lumen 218 is sized to accommodate the lead body within the lumen 218. In some examples, the needle 210 includes one or more markers 250 deployed along its length that are clearly visible when imaged by the particular technique being employed, and have at least some contrast with respect to the material from which the needle 210 is formed. In some examples, the needle 210 includes at least one imageable marker 250 corresponding in at least one of size, shape, number, and/or location to the at least one distal electrode of the lead body. In some examples, the at least one imageable marker 250 is configured to allow a physician or other user to determine placement within the patient of the at least one distal electrode of the lead body prior to implantation of the lead body within the patient.

In some embodiments, the one or more markings 250 form a marking pattern 250A that matches a contact or electrode pattern on the lead body, such that when the needle 210 is positioned and the lead body sits within the needle 210, the position of the distal contacts or electrodes relative to a nerve or other target (and the needle 210) can be ascertained readily. In this manner, in some examples, the lead body need not even be introduced into the needle 210 to allow a physician or other implanter to determine which distal contacts or electrodes will be most likely to stimulate particular portions of the targeted nerve, tissue, or other target. In some embodiments, the needle 210 can be marked with multiple marker patterns 250A, 250B, each marker pattern 250A, 250B mimicking a particular lead design so that one needle 210 may be used with many different lead models/types. In some examples, the needles 210 can be configured for use only with specific predetermined types of percutaneous leads. For instance, in some examples, various needles 210, each with different marker patterns 250A, 250B can be included and the physician or other implanter can select the particular needle 210 that is desired for a particular nerve or other target or the physician or other implanter can swap out one needle 210 for another needle 210 having a different marker pattern if that marker pattern turned out to be more desirable for the particular nerve or other target.

In some examples, the needle 210 includes a plurality of imageable markers 250, the plurality of imageable markers 250 corresponding in at least one of size, shape, number, and/or location to a plurality of distal electrodes of a first lead body. In further examples, the apparatus 200 includes another needle 210 including another plurality of imageable markers 250, the other plurality of imageable markers 250 corresponding in at least one of size, shape, number, and/or location to another plurality of distal electrodes of another, second lead body, wherein the other plurality of distal electrodes of the second lead body are configured differently than the plurality of distal electrodes of the first lead body. In some examples, the needle 210 can include a first marker pattern 250A that includes markers 250 that mimic a first distal electrode pattern of a lead body (for instance, a tightly-spaced, eight-electrode lead, as seen in FIG. 2A). In some examples, the needle 210 can include a second marker pattern 250B that includes markers 250 that mimic a second distal electrode pattern of a lead body (for instance, a widely-spaced, four-electrode lead, as seen in FIG. 2B). In various examples, the first and second marker patterns 250A, 250B can be included on the same needle 210 or on different needles 210. In various examples, the apparatus 200 can include one or more needles 210 including greater than or less than two marker patterns 250A, 250B, depending on how many distal contact or electrode patterns of how many lead bodies are desired to mimic.

In various examples, the at least one imageable marker 250 is configured to be imaged by one or more of various imaging techniques, including, but not limited to ultrasound, fluoroscopy, MRI, computerized tomography, x-ray, or the like. In some examples, the at least one imageable marker 250 is echogenic, the at least one imageable marker 250 being configured to be imaged by an ultrasound technique. In some examples, the at least one imageable marker 250 is configured to include increased echogenicity in a multitude of imaging planes which may be experienced targeting various tissue or nerves. In some examples, the at least one imageable marker 250 is configured to be imaged by a fluoroscopy technique.

Referring to FIGS. 3A-3D, and in some embodiments, an apparatus 300 is configured for targeted placement of a lead body (for instance, a lead body can be similar to the lead body 120 described herein) within a patient. In some examples, the lead body includes at least one distal electrode. In some examples, the apparatus 300 includes a needle 310 including a lumen 318 sized to accommodate the lead body within the lumen 318. In some examples, the needle 310 includes a needle head 312 at a proximal end of the needle 310. In some examples, the apparatus 300 further includes at least one stylet 340 insertable within the needle 310. In some examples, the stylet 340 includes a stylet head 342. In some examples, the stylet 340 includes an alignment feature 344 that is configured to interact with a complementary alignment feature 314 of the needle 310 to increase the likelihood that the stylet 340 is properly positioned, aligned, rotated, or otherwise located within the needle 310. In some examples, the stylet 340 includes a needle stylet. In some examples, the stylet 340 includes a lead stylet.

In some examples, the needle stylet 340 can include one or more imageable markings 350 that match different lead types. In some examples, the stylet 340 includes at least one imageable marker 350 corresponding in at least one of size, shape, number, and location to the at least one distal electrode of the lead body. In some examples, the at least one imageable marker 350 is configured to allow a user to determine placement within the patient of the at least one distal electrode of the lead body prior to implantation of the lead body within the patient. In some embodiments, different stylets 340 can be introduced for a fixed needle position such that each stylet 340 has markings 350 in different marker patterns 350A, 350B, 350C configured to match different distal contact or electrode patterns for various lead bodies. Thus, and in some embodiments, for a fixed needle position, multiple lead types may be "visually" tested simply by removing one version of the stylet 340 and replacing it with another stylet 340 until an optimal lead type has been determined.

In some embodiments, the one or more markings 350 form a marking pattern 350A that matches a contact or electrode pattern on the lead body, such that when the stylet 340 is positioned within the needle 310, the eventual position of the distal contacts or electrodes relative to a nerve or other target can be ascertained readily. In this manner, in some examples, the lead body need not even be introduced into the needle 310 to allow a physician or other implanter to determine which distal contacts or electrodes will be most likely to stimulate particular portions of the targeted nerve, tissue, or other target. In some embodiments, the stylet 340 can be marked with multiple marker patterns 350A, 350B, 350C, each marker pattern 350A, 350B, 350C mimicking a particular lead design so that one stylet 340 may be used with many different lead models/types. In some examples, the stylet 340 can be configured for use only with specific predetermined types of percutaneous leads. For instance, in some examples, various stylets 340, each with different marker patterns 350A, 350B, 350C can be included and the physician or other implanter can select the particular stylet 340 that is desired for a particular nerve or other target or the physician or other implanter can swap out one stylet 340 for another styler 340 having a different marker pattern if that marker pattern turned out to be more desirable for the particular nerve or other target.

In some examples, the stylet 340 includes a plurality of imageable markers 350, the plurality of imageable markers 350 corresponding in at least one of size, shape, number, and/or location to a plurality of distal electrodes of a first lead body. In further examples, the apparatus 300 includes another stylet 340 including another plurality of imageable markers 350, the other plurality of imageable markers 350 corresponding in at least one of size, shape, number, and/or location to another plurality of distal electrodes of another, second lead body, wherein the other plurality of distal electrodes of the second lead body are configured differently than the plurality of distal electrodes of the first lead body. In some examples, the stylet 340 can include a first marker pattern 350A that includes markers 350 that mimic a first distal electrode pattern of a lead body (for instance, a tightly-spaced, eight-electrode lead, as seen in FIG. 3B). In some examples, the stylet 340 can include a second marker pattern 350B that includes markers 350 that mimic a second distal electrode pattern of a lead body (for instance, a long-contact, tightly-spaced, eight-electrode lead, as seen in FIG. 3C). In some examples, the stylet 340 can include a third marker pattern 350C that includes markers 350 that mimic a third distal electrode pattern of a lead body (for instance, a widely-spaced, four-electrode lead, as seen in FIG. 3D). In various examples, the first, second, and third marker patterns 350A, 350B, 350C can be included on the same stylet 340 or on different stylets 340. In various examples, the apparatus 300 can include one or more stylets 340 including greater than or less than three marker patterns 350A, 350B, 350C, depending on how many distal contact or electrode patterns of how many lead bodies are desired to mimic.

In various examples, the at least one imageable marker 350 is configured to be imaged by one or more of various imaging techniques, including, but not limited to ultrasound, fluoroscopy, MRI, computerized tomography, x-ray, or the like. In some examples, the at least one imageable marker 350 is echogenic, the at least one imageable marker 350 being configured to be imaged by an ultrasound technique. In some examples, the at least one imageable marker 350 is configured to include increased echogenicity in a multitude of imaging planes which may be experienced targeting various tissue or nerves. In some examples, the at least one imageable marker 350 is configured to be imaged by a fluoroscopy technique.

Referring to FIG. 4, an apparatus 400 is configured for targeted placement of a lead body 420 within a patient. In some examples, the lead body 420 includes at least one distal electrode 430. In some examples, the apparatus 400 includes a needle 410 including a lumen 418 sized to accommodate the lead body 420 within the lumen 418. In some examples, the needle 410 includes a needle head 412 at a proximal end of the needle 410. In some examples, the apparatus 400 further includes at least one stylet 440 insertable within the needle 410. In some examples, the stylet 440 includes a stylet head 442. In some examples, the stylet 440 includes an alignment feature 444 that is configured to interact with a complementary alignment feature 414 of the needle 410 to increase the likelihood that the stylet 440 is properly positioned, aligned, rotated, or otherwise located within the needle 410. In some examples, the stylet 440 includes a needle stylet. In some examples, the stylet 440 includes a lead stylet.

In some embodiments, imageable markings 450 on the needle 410 can be made of an electrically conductive material which is electrically insulated from the material of the needle 410 (assuming the needle 410 itself is formed of an electrically conductive material). In some embodiments, the needle 410 has a connector 416 disposed thereon or attached thereto that allows for connection to a connector 472 of an external generator 470 (for instance, a stimulator 470 that the patient can use for trialing or permanently receiving therapeutic stimulation). In some examples, the at least one imageable marker 450 of the needle 410 includes a needle electrode 450 configured to perform a test stimulation. In this manner, and in some embodiments, the needle 410 can be appropriately positioned, stimulation can be delivered using the needle 410, and a position of the needle 410 can be adjusted to optimize the stimulation as needed, prior to placement of the lead body 420 within the needle 410 and removal of the needle 410.

In some examples, the needle 410 includes a plurality of imageable markers 450, the plurality of imageable markers 450 corresponding in at least one of size, shape, number, and/or location to a plurality of distal electrodes 430 of the lead body 420. In some examples, the needle 410 can include a marker pattern 450A that includes markers 450 that mimic a distal electrode pattern 430A of the lead body 420 (for instance, a widely-spaced, four-electrode lead, as seen in FIG. 4). In various examples, multiple marker patterns can be included on the same needle 410 or on different needles 410 in a manner similar to those described herein with respect to the apparatus 200. In various examples, the apparatus 400 can include one or more needles 410 including as many marker patterns as is desired to mimic distal contact or electrode patterns of lead bodies. In some examples, the imageable markers 450 can be included on the stylet 440 instead of or in addition to the needle 410.

In various examples, the at least one imageable marker 450 is configured to be imaged by one or more of various imaging techniques, including, but not limited to ultrasound, fluoroscopy, MRI, computerized tomography, x-ray, or the like. In some examples, the at least one imageable marker 450 is echogenic, the at least one imageable marker 450 being configured to be imaged by an ultrasound technique. In some examples, the at least one imageable marker 450 is configured to include increased echogenicity in a multitude of imaging planes which may be experienced targeting various tissue or nerves. In some examples, the at least one imageable marker 450 is configured to be imaged by a fluoroscopy technique.

Referring to FIGS. 5A and 5B, an apparatus 500 is configured for targeted placement of a lead body 520 within a patient. In some examples, the lead body 520 includes at least one distal electrode. In some examples, the apparatus 500 includes a needle 510 including a lumen 518 sized to accommodate the lead body 520 within the lumen 518. In some examples, the needle 510 includes a needle head 512 at a proximal end of the needle 510. In some examples, the needle 510 includes one or more imageable markings (for instance, similar to the imageable markings 250, 450 described herein) to mimic one or more distal contacts or electrodes of one or more lead bodies in a manner similar to those described herein (for instance, with respect to the apparatuses 200, 400).

In some embodiments, the needle 510 and the lead body include physical registration features 514, 522 that increase the likelihood that needle markings, whether only visually- and/or electrically-active, align adequately or to a sufficient degree with distal contacts or electrodes on the lead body 520. In some embodiments, the physical registration features 514, 522 permits the physician or other implanter to be confident that the position of the lead body 520 will be essentially the same as that identified by the needle 510. In some examples, the physical registration feature 514 of the needle 510 includes a lead lock feature 514 that selectively interacts with the lead body physical registration features 522. In some examples, the physical registration feature 522 of the lead body 520 includes a detent 522 that selectively interacts with the needle physical registration features 514. In some examples, the physical registration feature 514 of the needle 510 is hinged to the needle head 512 of the needle 510. In some examples, the physical registration feature 514 of the needle 510 includes a slot 516 configured to accept and lockably engage with the physical registration feature 522 of the lead body 520. In other examples, other forms of mating physical registration features are contemplated, provided that the other mating physical registration features function to increase the likelihood that needle markings align adequately or to a sufficient degree with distal contacts or electrodes on the lead body.

In some embodiments, different needles with different electrode configurations and numbers of electrodes are used to vet patient stimulation parameters before implanting a lead. In some embodiments, the needle helps the health care provider one pick a lead type, electrode configuration, and lead orientation that work best before the lead is implanted. In various embodiments, the spacing of electrodes on the needle can be varied, the number of electrodes can be varied, etc. In some embodiments, the needle can be used in determining optimal lead placement and stimulation parameters.

The present inventors have recognized various advantages of the subject matter described herein. For instance, in some examples, the apparatuses, systems, and methods described herein can be used to target placement of an implantable device within a patient to allow for better placement of the implantable device and potentially improve performance of the implantable device in treating the patient. In various examples, the apparatuses, systems, and methods described herein are considered advantageous in that they allow for targeting placement of an electrical stimulation lead. Additionally, in various examples, the apparatuses, systems, and methods described herein include targeting using various imaging techniques to allow for continuous real-time location information. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. An apparatus for targeted placement of a lead body within a patient, the apparatus comprising:
   the lead body including a plurality of distal electrodes;
   a needle including a lumen sized to accommodate the lead body within the lumen, wherein the lead body is configured to be insertable within and passed through the lumen of the needle during placement of the lead body within the patient; and
   a stylet that is configured to be insertable within the lumen of the needle, wherein the stylet includes a plurality of imageable markers that, with the stylet inserted within the lumen of the needle, are imageable through the needle and correspond in size, shape, and location to the plurality of distal electrodes of the lead body, the plurality of imageable markers being configured to allow a user to determine placement within the patient of the plurality of distal electrodes of the lead body prior to the lead body being passed through the lumen of the needle during placement and implantation of the lead body within the patient, wherein the stylet is inserted within and removed from the lumen of the needle prior to insertion of the lead body within the lumen of the needle.

2. The apparatus of claim 1, wherein the needle includes a needle electrode configured to perform a test stimulation.

3. The apparatus of claim 1, wherein the lead body is a first lead body, the apparatus comprising a second stylet including a second plurality of imageable markers that are imageable through the needle, the second plurality of imageable markers corresponding in size, shape, and location to a second plurality of distal electrodes of a second lead body, the second plurality of distal electrodes of the second lead body being configured differently than the plurality of distal electrodes of the first lead body.

4. The apparatus of claim 1, wherein the plurality of imageable markers is echogenic, the plurality of imageable markers being configured to be imaged by an ultrasound technique.

5. The apparatus of claim 1, wherein the plurality of imageable markers is configured to be imaged by a fluoroscopy technique.

6. The apparatus of claim 1, wherein the needle includes a needle registration feature and the lead body includes a lead body registration feature, wherein, with the lead body properly disposed within the lumen of the needle, the needle registration feature corresponds with the lead body registration feature.

7. The apparatus of claim 6, wherein:
   the needle registration feature includes a lead lock feature hinged to a needle head of the needle, the lead lock feature including a slot; and
   the lead body registration feature includes a detent disposed on the lead body, the lead lock feature being configured to pivot to accept the detent of the lead body within the slot of the lead lock feature with the lead body properly disposed within the lumen of the needle.

8. The apparatus of claim 1, wherein the stylet includes a stylet alignment feature and the needle includes a needle alignment feature, the needle alignment feature being complementary to the stylet alignment feature, wherein the needle alignment feature and the stylet alignment feature are configured to interact with the stylet properly positioned within the needle.

9. The apparatus of claim 8, wherein:
   the stylet alignment feature includes a protrusion extending distally from a stylet head; and
   the needle alignment feature includes an indentation disposed within a needle head, the indentation being complementary to the protrusion, such that the protrusion is sized and shaped to fit within the indentation with the stylet properly positioned within the needle.

10. An apparatus for targeted placement of a first lead body within a patient, the apparatus comprising:
    the first lead body including a first plurality of distal electrodes;
    a first single-lumen needle including a single lumen sized to accommodate the first lead body within the single lumen, wherein the first lead body is configured to be insertable within and passed through the single lumen of the first single-lumen needle during placement of the first lead body within the patient; and
    a first stylet that is configured to be insertable within the single lumen of the first single-lumen needle, wherein the first stylet includes a first plurality of imageable markers that, with the first stylet inserted within the single lumen of the first single-lumen needle, are imageable through the first single-lumen needle and correspond in size, shape, spacing, and location to the first plurality of distal electrodes of the first lead body, the first plurality of imageable markers being configured to allow a user to determine placement within the patient of the first plurality of distal electrodes of the first lead body prior to the first lead body being passed through the single lumen of the first single-lumen needle during placement and implantation of the first lead body within the patient, wherein the first stylet is inserted within and removed from the single lumen of the first single-lumen needle prior to insertion of the first lead body within the single lumen of the first single-lumen needle.

11. The apparatus of claim 10, wherein the first plurality of imageable markers is echogenic, the first plurality of imageable markers being configured to be imaged by an ultrasound technique.

12. The apparatus of claim 10, wherein the first plurality of imageable markers is configured to be imaged by a fluoroscopy technique.

13. The apparatus of claim 10, wherein the first single-lumen needle includes a needle electrode configured to perform a test stimulation.

14. The apparatus of claim 10, wherein the first stylet includes the first plurality of imageable markers, the apparatus including a second stylet interchangeable with the first stylet, the second stylet including a second plurality of imageable markers differently configured in at least one of size, shape, spacing, and location from the first plurality of imageable markers of the first stylet, wherein the second plurality of imageable markers are imageable through the first single-lumen needle and correspond in size, shape, spacing, and location to a second plurality of distal electrodes of a second lead body.

15. The apparatus of claim 10, wherein the first stylet includes a first stylet alignment feature and the first single-lumen needle includes a first needle alignment feature, the first stylet alignment feature including a protrusion extending distally from a first stylet head, the first needle alignment feature including an indentation disposed within a first needle head, the indentation being complementary to the protrusion, such that the protrusion is sized and shaped to fit within the indentation with the first stylet properly positioned within the first single-lumen needle.

16. The apparatus of claim 10, wherein the first single-lumen needle includes a needle registration feature including a lead lock feature hinged to a first needle head of the first single-lumen needle, the lead lock feature including a slot, the first lead body including a lead body registration feature including a detent disposed on the first lead body, the lead lock feature being configured to pivot to accept the detent of the first lead body within the slot of the lead lock feature with the first lead body properly disposed within the single lumen of the first single-lumen needle.

17. An apparatus for targeted placement of a first lead body within a patient, the apparatus comprising:
the first lead body including a first plurality of distal electrodes;
a first single-lumen needle including a single lumen sized to accommodate the first lead body within the single lumen, wherein the first lead body is configured to be insertable within and passed through the single lumen of the first single-lumen needle during placement of the first lead body within the patient; and
a first stylet that is configured to be insertable within the single lumen of the first single-lumen needle, wherein the first stylet includes a first plurality of echogenic markers that, with the first stylet inserted within the single lumen of the first single-lumen needle, are ultrasonically detectable through the first single-lumen needle and correspond in spacing and location to the first plurality of distal electrodes of the first lead body, the first plurality of echogenic markers being configured to allow a user to image the first plurality of echogenic markers by an ultrasonic technique to determine placement within the patient of the first plurality of distal electrodes of the first lead body prior to the first lead body being passed through the single lumen of the first single-lumen needle during placement and implantation of the first lead body within the patient, wherein the first stylet is inserted within and removed from the single lumen of the first single-lumen needle prior to insertion of the first lead body within the single lumen of the first single-lumen needle.

18. The apparatus of claim 17, wherein the first single-lumen needle includes a needle electrode configured to perform a test stimulation.

19. The apparatus of claim 17, wherein the first stylet includes the first plurality of echogenic markers, the apparatus including a second stylet that is interchangeable with the first stylet, the second stylet including a second plurality of echogenic markers differently configured in at least one of spacing and location from the first plurality of echogenic markers of the first stylet, wherein the second plurality of echogenic markers are ultrasonically detectable through the first single-lumen needle and correspond in spacing and location to a second plurality of distal electrodes of a second lead body.

20. The apparatus of claim 17, wherein the first single-lumen needle includes a needle registration feature including a lead lock feature hinged to a first needle head of the first single-lumen needle, the lead lock feature including a slot, the first lead body including a lead body registration feature including a detent disposed on the first lead body, the lead lock feature being configured to pivot to accept the detent of the first lead body within the slot of the lead lock feature with the first lead body properly disposed within the single lumen of the first single-lumen needle.

* * * * *